United States Patent [19]

Gu et al.

[11] Patent Number: 4,940,060
[45] Date of Patent: Jul. 10, 1990

[54] APPARATUS FOR DETECTING BIOELECTRIC SIGNALS

[76] Inventors: Hansen Gu; Dumin Wu, both of Building 18, HongXu Road, Shanghai, China

[21] Appl. No.: 94,621

[22] Filed: Sep. 9, 1987

[30] Foreign Application Priority Data

Sep. 9, 1986 [CN] China .................... 86105980

[51] Int. Cl.$^5$ ........................... A61H 39/02
[52] U.S. Cl. ........................... 128/735; 128/741; 128/907
[58] Field of Search ............... 128/734–735, 128/907, 419 R, 420, 421–422, 423 R, 741

[56] References Cited

U.S. PATENT DOCUMENTS

| | | | |
|---|---|---|---|
| 2,716,979 | 9/1955 | Pouret | 128/735 |
| 3,785,368 | 1/1974 | McCarthy et al. | 128/734 X |
| 3,897,789 | 8/1975 | Blanchard | 128/907 X |
| 3,900,020 | 8/1975 | Lock | 128/907 X |
| 3,980,077 | 9/1976 | Shaw, IV | 128/734 |
| 4,016,870 | 4/1977 | Lock | 128/735 |
| 4,112,923 | 9/1978 | Tomecek | 128/735 X |
| 4,319,584 | 3/1982 | McCall | 128/907 X |
| 4,408,617 | 10/1983 | Auguste | 128/907 X |
| 4,503,863 | 3/1985 | Katims | 128/741 |
| 4,694,840 | 9/1987 | Kairis et al. | 128/735 |

FOREIGN PATENT DOCUMENTS

| | | | |
|---|---|---|---|
| 8401516 | 4/1984 | PCT Int'l Appl. | 128/734 |
| 0001317 | 2/1986 | PCT Int'l Appl. | 128/734 |
| 1277965 | 12/1986 | U.S.S.R. | 128/907 |

Primary Examiner—Angela D. Sykes

[57] ABSTRACT

An apparatus for detecting bioelectric signals according to the present invention, comprises: a detecting electrode, a reference electrode, a stimulating signal generating circuit, a micro-current amplifying circuit, a signal processing circuit and an output device. The detecting apparatus applies a stimulating voltage in the range of 0.5–3.0 V to a reference acupoint on human or animal body via the reference electrode, and detects simultaneously the response current in the range $10^{-11}$–$10^{-4}$ A at different acupressure points on the body with the detecting electrode urged against the acupressure point, then the time response of the current is processed by the signal processing circuit to obtain the useful information for diagnosing diseases and verifying the therapeutic effects.

18 Claims, 14 Drawing Sheets

APPARATUS FOR DETECTING BIOELECTRIC SIGNALS

FIELD OF THE INVENTION

The present invention relates to an apparatus for detecting bioelectric signals and, more particularly, to an apparatus which can apply an electric stimulating signal to a certain acupressure point ("acupoint") on the surface of a human or animal body and detect simultaneously the response of the body to this stimulating signal, thereby to obtain characteristic information about the distribution and movement of the bioelectric field within the living body, diagnose diseases, monitor the health status and verify the therapeutic effects of a treatment.

BACKGROUND OF THE INVENTION

Recently, basing on the field theory, the information techniques and the theory of the traditional Chinese medicine, especially the theory of channels and collaterals, the Chinese academic community has made extensive researches and a great deal of experiments on the vital information, one of the most important vital characteristics of a living body. Particularly, by means of modern detecting equipments, different measuring tests were made on "Fa Gong", an energy emitting phenomena performed by a "Qi Gong" expert, a deep breathing exercises expert, and on isotopic tracing of the channels and collaterals, resulting in remarkable achievements. These research results were reported on "NATURE JOURNAL" Vol. 3, No. 8, Aug., 1980, PP 563-566, entitled "A Preliminary Study on the Dispatching and Accepting of Vitalist-Code by Human Body", and Vol. 3 No. 9, Sept., 1980, PP 681-682, entitled "Experimental Research of the Acupuncture Points along the Pericardium Meridian" published by Shanghai Science and Technology Publishing House, and "SCIENCE YEAR BOOK" 1981, PP 1.34-1.41, entitled "The Research Reproduction and Application of Specific Life Information", published also by Shanghai Science and Technology Publishing House. The contents of these articles are incorporated herewith by reference.

According to the theory of physics, the physical world manifests itself in two kinds of matter, one with static mass while the other without static mass but with energy (different kinds of field). These two kinds of matter are highly correlated and any one with static mass possesses its own natural resonance frequency. A living body can also be treated as a morphology system made up of cells, tissues and organs, as well as an information system made up of different kind of field matter, such as cell potential, electrocardiographic signals, electroencephalographic signals and various kinds of radiation. The two systems interact on each other and coexist within the same living body. The channels and collaterals system of the traditional Chinese medicine, if analysed according to the principles of its performance, is an inseparable part of the vital information system of a human body. The distribution and movement of the field matter of the vital information system will be changed by the abnormality of any tissue or organ of a living body, no matter whether it is a functional disorder or an organic change. Therefore, important information about the health status of a living body can be obtained by detecting the distribution and movement of the field matter of the vital information system.

In clinical practice of the traditional Chinese medicine, it has long been recognized that when some kind of disorder happened to an organ within a human body, along the channels and collaterals corresponding to this organ can often be found some specific acupoints (such as the ones located on hands, feet or limbs) which manifest high sensitivity to, for example, touch and acupuncture, and the acupuncture treatment on such acupoints can almost always lead to a satisfied result. This phenomenon can be well explained by the theory of channels and collaterals of the traditional Chinese medicine and it is often used in the clinical practice for diagnostic purposes. However, there exist differences between individuals for this phenomenon of acupoints' sensitivity, and on the other hand, like all the other phenomena relating to the channels, collaterals and acupoints, the clinical use of this phenomenon relies wholly upon the patient's stated awareness and there is no physical means for quantitative detection and evaluation, which has seriously restricted its clinical use. Accordingly, the detection of the acupoints by modern detecting means has become a more and more interesting research field.

In the prior art, there are different kinds of devices for detecting acupoints and obtaining the characteristic information therefrom. These devices can be used to detect at different points on the body surface the changes of different physical parameters, such as resistance, electrical potential, magnetic field, temperature, sensitivity of the point to the pressure, etc, and to locate the points with abnormal values. The diagnosis and treatment of diseases can be made according to the quantitative changes of these physical parameters.

It is known in the prior art that when some kind of disease happened to a person, the decrease of skin resistance or increase of electric potential can be detected at some specific points on the skin of the patient, and devices have been designed according to this discovery for detecting skin resistance or electric potential at specific points. However, since the intensity of the bioelectric field within a living body is very low, the differences of the distribution and movement of this electric field between its normal and abnormal states, especially for those at their early stage, are very small. In addition, because of the existence of the individual differences and the environmental interferences, it is difficult to make a detection of this bioelectric field and more difficult to obtain useful information therefrom. In this case, if only a receiving-type or passive apparatus is used for detecting the characteristic values of this bioelectric field, such as using a highly sensitive potentiometer to sense the tiny variation of the potential at the points, the detecting sensitivity and the interference shielding capability of the apparatus must be very high. All environmental interferences should be under strict control to overcome the above-mentioned difficulties and get the useful detecting results. These constraints make the detecting apparatus and process very complicated and expensive, and it is still difficult to distinguish the tiny variations of the potential at the points from environmental interference. For these reasons, statistically meaningful detecting results can not be obtained for diagnosing the diseases at their early stage. For solving the problems, apparatus was designed for detecting the change of resistance between points to identify the specific points. This was done by way of applying a voltage to a living body and detecting simultaneously the current through the points to obtain useful information therefrom. This kind of detection has a much lower requirement with respect to the physical means and environmental control, so it can be easily used in different circumstances. However, in this kind of detection both the relatively high stimulating voltage (usually 10–20 V or more) and strong pressure applied to the point by the electrodes have formed an external stimulation to the points and changed artificially the normal state of the distribution and movement of the bioelectric field within the living body. Therefore, the interference to a living body produced by the detection itself have made impossible the gathering of useful information which reflects pathological changes within a living body.

To solve the problems in prior art, the present inventors have suggested that the theory of channels and collaterals, and the acupoints known to traditional Chinese medicine, reflect certain special principles about the distribution and movement of the electromagnetic field within human body, and form an unseparable part of the vital information system of human body. If proper means can be provided to avoid both the environmental and detective interference with the electro-magnetic field within the human body, the important information which reflects the state of the channels and collaterals system and the vital information system, can be obtained by detecting electric parameters at different points. This information can then be used for diagnosing diseases and verifying the curative effects of a therapeutic process.

SUMMARY OF THE INVENTION

The present invention provides an apparatus for detecting bioelectric signals which is reduced to practice, based on the above conception, by applying a stimulating signal of proper amplitude to specific acupoints on human or animal body and detecting simultaneously the response of the body to the signal, thereby obtaining the important vital information through analysis of the amplitude versus time response characteristics of the signal, and using it in diagnosing and treating diseases.

On the basis of comprehensive experiments, the amplitude and waveform of the stimulating signal of the present invention is selected and the way of applying the same to a living body is decided to reach a good balance between the bioelectric signal of the living body and the stimulating signal of the apparatus. In this way the latter will not cause serious interference with distribution and movement of the electro-magnetic field within the living body, and the response of the body to this signal can reflect the important vital information which is significantly meaningful in statistic sense for distinguishing diseases from health, especially for those at their early stage.

The body's response to the stimulating signals of the present invention is a current signal of a very small amplitude within a range of $10^{-4}$ – $10^{-11}$ A, corresponding to different kinds of pathological disorders. Therefore, it is necessary for the apparatus of the present invention to adopt an amplifier which can amplify a micro-current as small as $10^{-12}$ ampere, and the working range thereof should be from $10^{-11}$ A to $10^{-4}$ A. To meet such a requirement of the current's varying range, a logarithmic micro-current amplifier or a linear micro-current amplifier exponentially ranged should be preferably adapted, and this amplifier should possess a good anti-interference capability during the detecting process when its input probes contact the human body directly.

The micro-current signal of a living body responsive to the stimulating signal of the invention presents an amplitude versus time characteristic curve, in which specific relationships exist relating the shape of the curve detected at certain acupoints to the disease suffered by the body. For this reason, both the amplitude of the signal and the shape of the time response curve are useful for diagnosing diseases. According to these characteristics, the apparatus of the invention comprises a signal processing circuit to process the response signals. In addition, the output device of the apparatus should be able to display such a time response curve.

When the apparatus of the invention is used for detecting acupoints, especially when the noninvasive detecting electrodes of the invention are used in detecting, the different pressures applied to the skin point by electrodes will cause different influences on the physical state of the local skin and thereby change the skin's resistivity, local blood microcirculation, etc, which will in turn influence the accuracy of the detection. On the other hand, a very strong pressure per se can become a strong external stimulation to the acupoint and change the state of the local bioelectric field. In order to guarantee an accurate detection, the pressure of the electrode applied to acupoints should be kept as small as possible and it is also necessary to keep the value of this pressure constant for all detection. In this way, the detection can be performed under substantially the same conditions for different persons and at different moments. Additionally, the environmental factors, such as temperature, humidity, etc, can also influence the skin's resistivity, and affect the comparability of the detecting results. The pressure applied to the acupoints by the electrodes is kept constant during detection by way of an adjustable elastic structure specially designed for the electrodes of the invention, and changes in the environmental temperature and humidity can be properly compensated by adjusting the pressure.

As mentioned before, two problems existing during the acupoint detection have been solved by the detecting apparatus of the present invention. On the one hand, the interference produced by the detecting per se on the state of distribution of the electro-magnetic field within a living body is kept as small as possible by way of a strict restriction of the stimulation to the skin points by stimulating signals and detecting electrodes. On the other hand, the amount of information obtained during detection is significantly increased by adopting a wide range micro-current amplifier, a signal processing circuit for processing the time response curve of the micro-current signal, and an output device for displaying the results. In this way, the apparatus of the present invention can detect much important information which can not be obtained by any of the prior art apparatus.

According to a preferred embodiment of the apparatus for detecting bioelectric signals of the present invention, the apparatus comprises: a detecting electrode; a reference electrode; a stimulating signal generating circuit connected to the reference electrode; a micro-current amplifying circuit connected to the detecting electrode; a signal processing circuit, composed of a flip-flop, an adjustable delay circuit, and a sample-and-hold circuit which is connected to the amplifying circuit; and an output device which is connected to the signal processing circuit. The apparatus applies a stimulating voltage having a specific amplitude between a reference point and another point to be detected via the reference and detecting electrodes, respectively, to form an electrical loop, and the micro-current flowing in the loop is amplified by the micro-current amplifying circuit and then provided to the signal processing circuit, wherein the current signal is sampled according to a predetermined delay time. The sampled results are displayed, recorded and/or stored by the output device.

According to another prefered embodiment of the apparatus of the invention, the apparatus comprises: a detecting electrode; a reference electrode; a stimulating signal generating circuit connected to the reference electrode; a mirco-current amplifying circuit connected to the detecting electrode; a signal processing circuit comprising an analog-to-digital (A/D) converter, a central processing unit (CPU), a memory and an input-/output (I/O) interface connected to the amplifying circuit, a control board and an output device both connected to the I/O interface. The apparatus applies a stimulating voltage of specific amplitude to a reference point and another point to be detected via the reference and detecting electrodes, respectively, to form an electrical loop, and the micro-current signal is amplified by the micro-current amplifying circuit and then provided to the signal processing circuit, wherein real time processing is performed on the amplified micro-current. The time response curve, the characteristic parameters of the curve and the relevant information inputted through the control board may be displayed, recorded and stored by the output device, or provided for further processing, such as statistical analysis, comparison with normal values, etc.

According to yet another preferred embodiment of the apparatus of the invention, the apparatus comprises: a detecting electrode; a reference electrode; a stimulating signal generating circuit connected to the reference electrode; a micro-current amplifying circuit connected to the detecting electrode; at least one pair of parallel comparison circuits connected to the output terminal of the amplifying circuit; and at least one pair of display devices connected to the comparison circuits, respectively. The apparatus applies a stimulating voltage of specific amplitude between a reference point and an acupressure point ("acupoint") via the reference and detecting electrodes, respectively, to form an electrical loop, and the micro-current signal flowing in this loop is amplified by the micro-current amplifying circuit. When the detected intensity of the micro-current is beyond a certain lower threshold value, one of the comparison circuits connected to the amplifying circuit works to drive the display device (such as, for example, a LED) connected to it to show the detected result illustratively. When the detected current intensity is below a certain upper threshold value, the other comparison circuit works to drive the other display device. When the detected intensity of the current is between the upper and lower threshold values, namely, is within the normal range, the two parallel comparison circuits work together to drive both of the display devices simultaneously, so as to qualitatively show the detected result.

When the apparatus of the invention is used in actual detection, the reference electrode can be put on a reference point located on the centerline of the human body under detection, such as Yin-Tang point on forehead, Bai-Hui point on top of the head, the Da-Zhui point at back of the neck, etc, to apply the stimulating voltage thereon, while the detecting electrode is used to detect, one by one at acupressure points all over the body, the information from each of the acupressure points.

One object of the invention is to provide an apparatus for detecting the distribution and movement state of the bioelectric field of living tissue to obtain the characteristic parameters therefrom.

Another object of the invention is to provide an apparatus for detecting bioelectric signals to obtain the information important for diagnosing diseases and verifying the therapeutic effects of a treatment by way of point detection on human or animal body, thereby to provide a new approach for medical diagnosis and verification.

Yet another object of the invention is to provide a detecting apparatus which can meet the requirements of the theory and clinical practice of the traditional Chinese medicine, to fulfil the diagnosis of diseases and verification of therapeutic effects according to electrical characteristic parameters of the channels, collaterals and acupoints, thereby to provide a sound basis for making the diagnosis method of the traditional Chinese medicine objective, quantitative and automatic.

The other objects, features and advantages of the invention will become more apparent in the following detailed description of the preferred embodiments of the invention with reference to the accompanying drawings, wherein like reference numerals represent like components or features.

DETAILED DESCRIPTION OF THE INVENTION

The detailed description of the conception and the prefered embodiments of the apparatus for detecting bioelectric signals according to the present invention is made hereinbelow with reference to the accompanying drawings.

Figure 1:
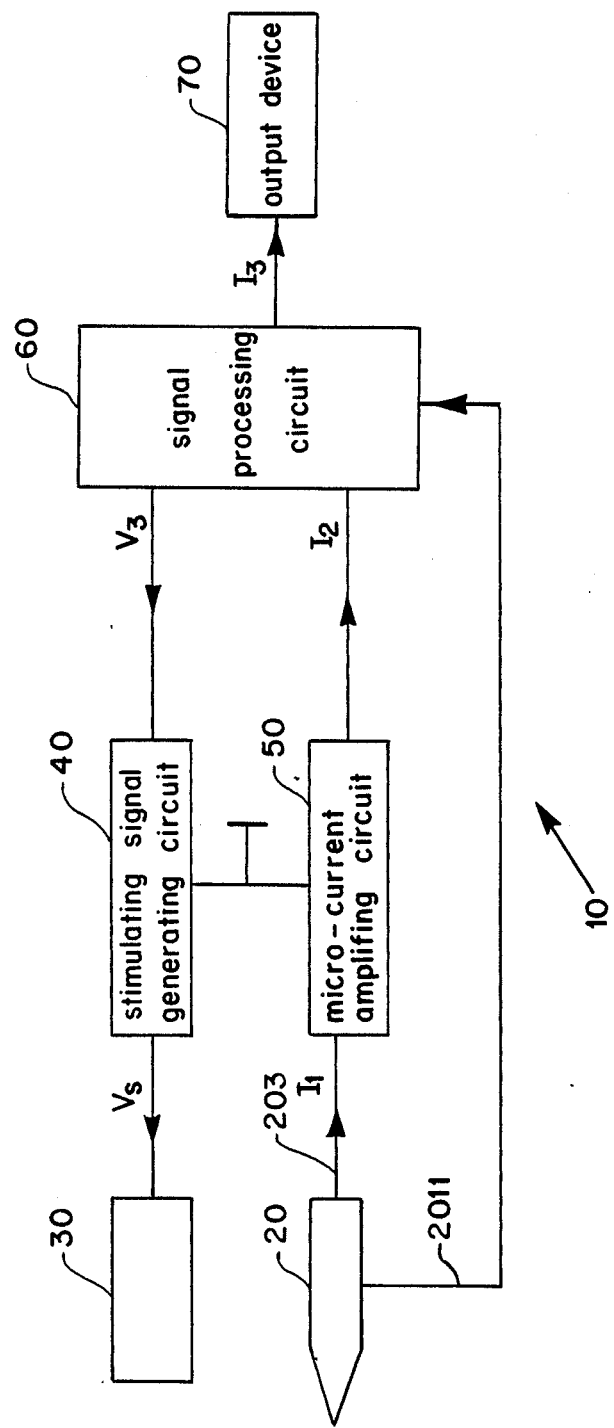
FIG. 1 is a block diagram illustrating the structure of the apparatus according to the present invention.

Referring to FIG. 1, there is shown the block diagram of the detecting apparatus of the invention. In FIG. 1, numeral 10 represents the apparatus as a whole; numeral 20 indicates a detecting electrode having a signal line 203 and a control line 2011; numeral 30 indicates a reference electrode made of a metal sheet, which can be any kind of conventional detecting electrode for medical use; numeral 40 indicates a stimulating signal generating circuit; numeral 50 indicates a micro-current amplifying circuit; numeral 60 indicates a signal processing circuit; and numeral 70 indicates an output device. The detailed description of the above circuits will be given hereinbelow.

Figure 2:
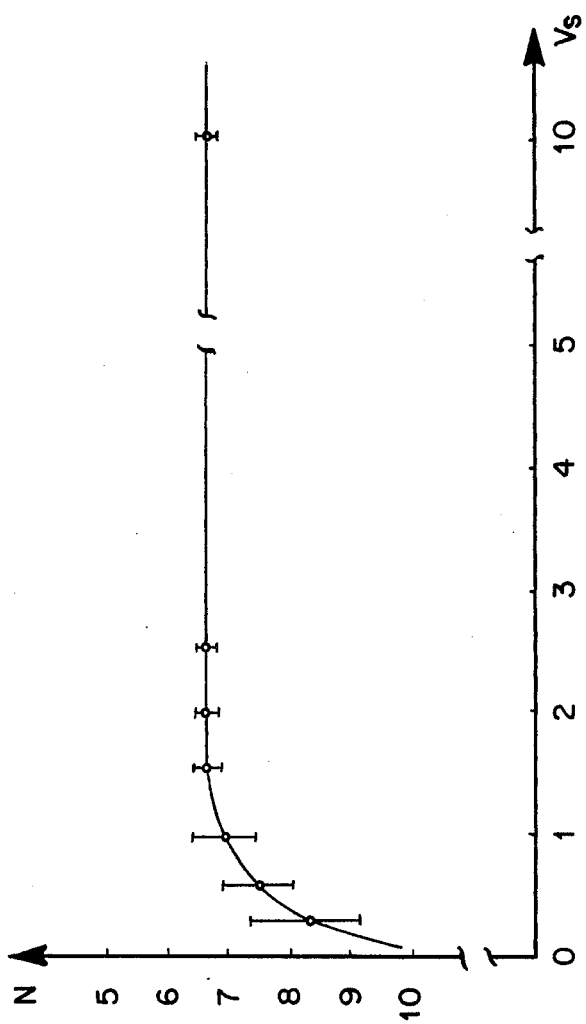
FIG. 2 is a diagram showing the statistical results of the response currents detected under different stimulating voltages applied to healthy people.

It is shown in FIG. 2 the statistical distribution of the values of response currents versus stimulating voltages, detected under the same detecting conditions from a group of healthy people by using the apparatus of the invention, wherein the data are obtained by putting the reference electrode at the Yin-Tang point on forehead and applying different stimulating voltages thereon, and at the same time using the detecting electrode sensing repeatedly the same group of points. In FIG. 2, the abscissa indicates the values of the stimulating voltage Vs in term of volts, and the ordinate indicates the negative logarithmic value N of the detected response current $I_1$ in term of amperes, wherein $N = -\log I_1$, for example, when $I_1 = 10^{-7}$ A, $N = 7$. It is shown in FIG. 2 that when the stimulating voltage Vs is larger than 3.0 V, the dispersion of the detected values is small, the detected results are stable, that means they are not influenced by increasing the stimulating voltage. When the stimulating voltage is less than 1.0 V, the detected value of the current will be changed significantly with the changing of the voltage, and on the other hand, the dispersion of the detected results of the same group of people will be significantly increased, that means the detection is seriously influenced by the environmental factors. It can be seen in FIG. 2 that if the stimulating voltage is too small (less than 1.0 V), the dispersion of the detected values will be large and it is difficult to make statistic processing and obtain the useful information for diagnosing diseases.

Figure 3:
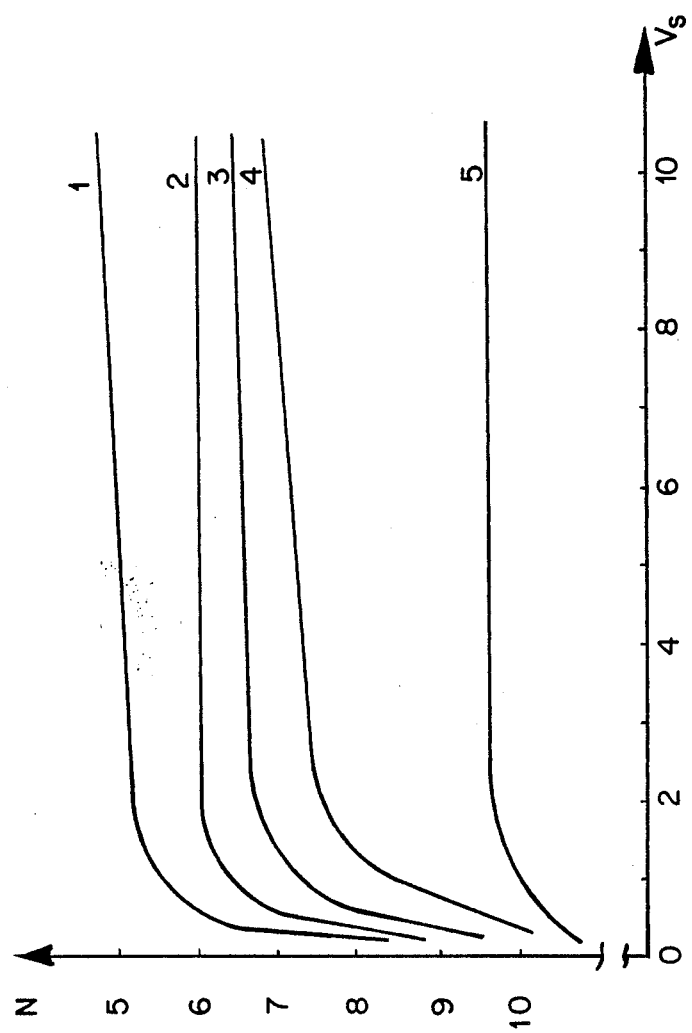
FIG. 3 shows the relationship between stimulating voltages and response currents corresponding to people having different health problems.

Referring to FIG. 3, there is shown the curves illustrating the relationship between the different stimulating voltages and the averaged values of the negative logarithm of the response currents detected from several groups of patients. The detection is made by using, under the same conditions, the detecting apparatus of the invention to several groups of patients having different diseases that have been diagnosed by other clinical means. In FIG. 3, the abscissa and ordinate represent the same thing as that of FIG. 2. Curve 3 is graph of the averaged value of the statistic distribution shown in FIG. 2. Curve 1 is detected from a group of patients having manic mental disorders, curve 2 is detected from a group of patients having slight autonomic nerve system disorders, curve 4 is detected from a group of patients having slight metabolic disorders; and curve 5 is detected from a group of patients having cancers at advanced stage. It can be seen from the curves of FIG. 3 that as the stimulating voltage is getting increased, the value detected from the patients having serious problems (shown by curves 1 and 5) keep relatively big differences with that of healthy people (shown by curve 3), but the values detected from patients having slight problems (shown by curves 2 and 4) are getting close to that of healthy people (shown by curve 3). If the dispersion of the practically detected values is taken into consideration (such as shown by FIG. 2), it is difficult to distinguish the detected values of the healthy people from that of the patients having slight disorders. In other words, when the stimulating voltage is relatively too strong, the signals corresponding to the slight disorders will be "drowned" by this strong external signal, so as make the diagnosis of diseases at their early stage impossible. It can be seen in FIG. 3 that when the stimulating voltage Vs is within the range of 1.0–3.0 V, the differences between each of the curves are most distinguishable.

It can be concluded by combining the data shown in FIGS. 2 and 3 that in detecting the electrical signals of a human body by the apparatus of the invention, the stimulating voltage should be selected from the range of 1.0–3.0 V, preferably 2.0 V.

Figure 4:
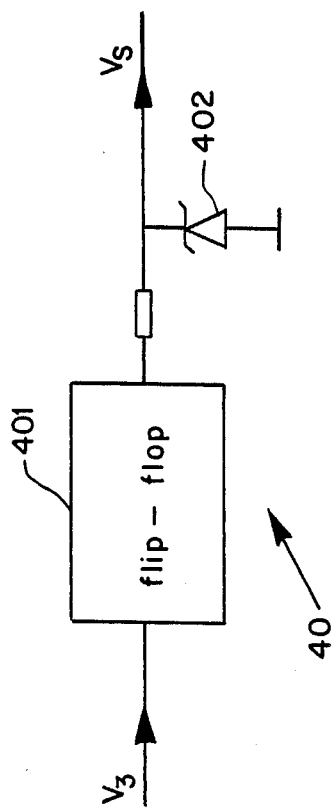
FIG. 4 shows an exemplary embodiment of the stimulating signal generating circuit 40 shown in FIG. 1.

Referring to FIG. 4, there is shown an exemplary embodiment of the stimulating signal generating circuit 40 shown in FIG. 1. In FIG. 4, numeral 401 indicates a flip-flop which, under the control of the activating signal $V_3$ provided by the signal processing circuit, generates at its output terminal a step signal having a very steep leading edge and adjustable width, the amplitude of this step signal is clamped to 2.0 V by a clamping diode 402, then this step signal is provided to the reference electrode as the stimulating signal Vs. The fluctuation of the amplitude of the stimulating voltage Vs is kept less than 1% by using the clamping diode 402 to avoid the fluctuation of the detected current caused thereby. It is obvious according to the principles shown by FIG. 4 that any conventional stabilized voltage source can be used as the stimulating signal generating circuit of this apparatus, and if a step signal with a very steep leading edge is generated under the control of the signal processing circuit, a more accurate current detection can be performed.

Figure 5A:
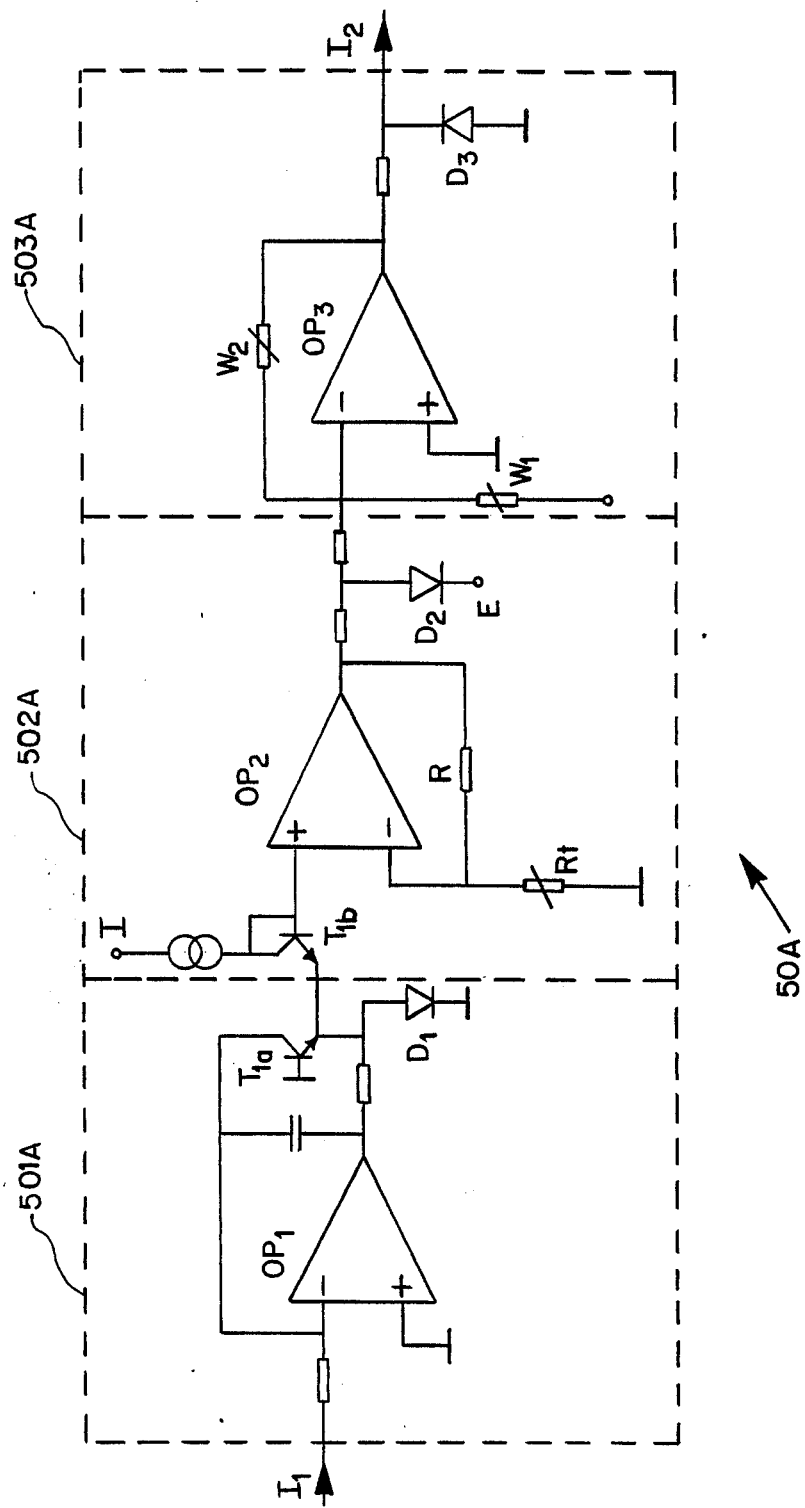
FIGS. 5A-5B show respectively two different embodiments of the micro-current amplifying circuit 50 shown in FIG. 1.

Referring to FIG. 5A, there is shown an embodiment of the micro-current amplifying circuit 50 shown in FIG. 1. In FIG. 5A, numeral 50A represents the amplifying circuit as a whole; the dash line block 501A indicates a logarithmic micro-current amplifier formed by an operational amplifier $OP_1$ and a transistor T1a; the dash line block 502A indicates a temperature compensating circuit, wherein I is a constant current source, T1b is a transistor forming a couple with T1a of 501A, whereby T1b compensates the parallel part of the temperature drift of T1a, while Rt and R compensate the slope part of the temperature drift of T1a and control the gain of this compensating circuit. The dash line block 503A indicates an inverting circuit wherein the amplified current signal is inverted by $OP_3$, $W_1$ is a potentiometer for adjusting the zero point of the output and $W_2$ is another potentiometer for adjusting the full range of the output. In FIG. 5A, diodes $D_1$, $D_2$ and $D_3$ are used for clamping, respectively. When the logarithmic micro-current amplifier shown in FIG. 5A is used for amplifying a micro-current signal in the range of $10^{-11} - 10^{-4}$ A, it is required that the minimum operational current of the operational amplifier $OP_1$ be $10^{-12}$ A. This requirement can be met by prior art amplifiers, so it will not be further explained.

Figure 5B:
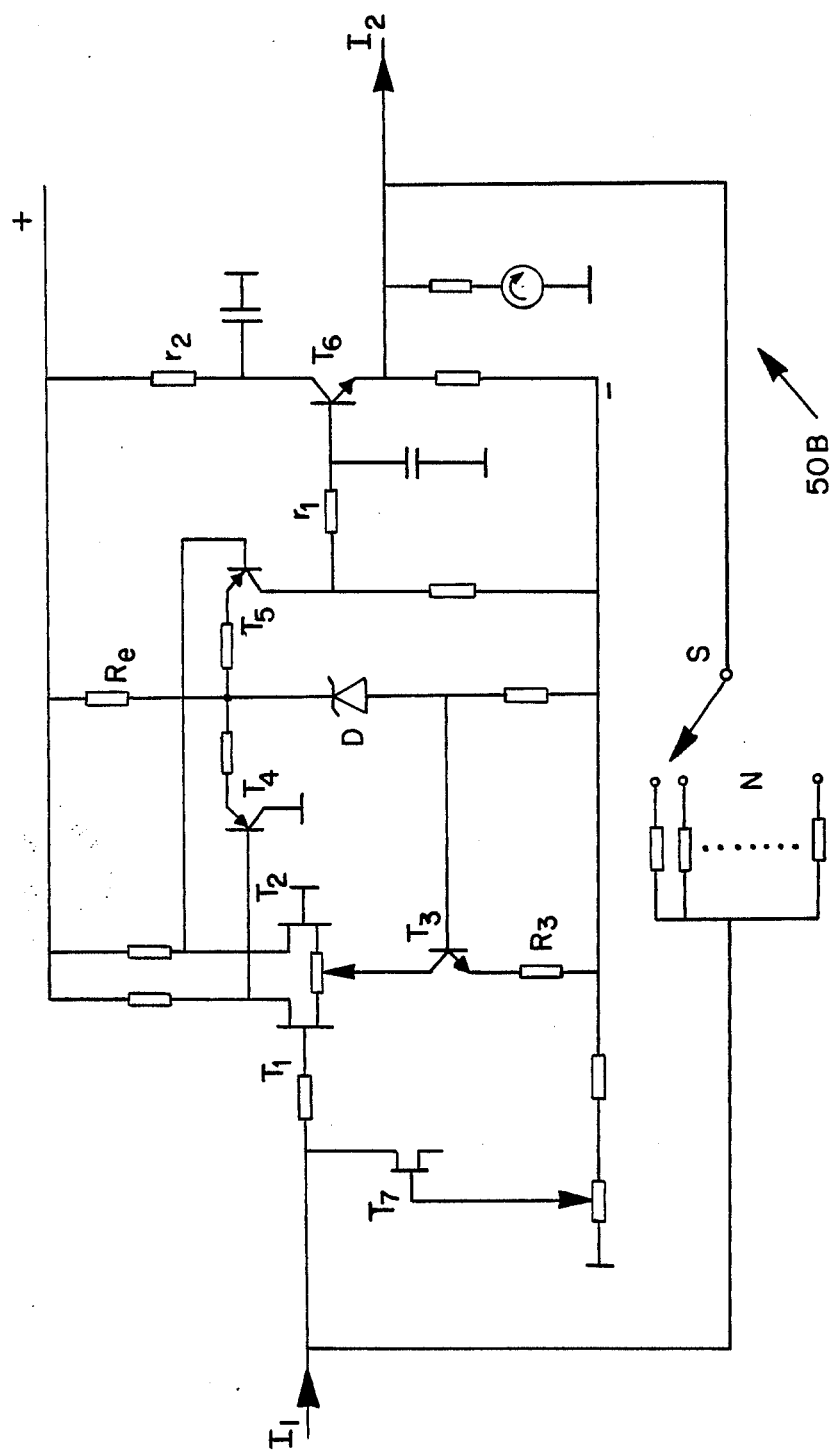

Referring to FIG. 5B, there is shown another embodiment of the micro-current amplifying circuit 50 shown in FIG. 1. In FIG. 5B, numeral 50 B represents the amplifying circuit as a whole. $T_1$ and $T_2$ are junction field effect transistors which form the differential input stage of this circuit, while $T_3$ and $R_3$ form the equivalent impedance of the constant current source of this differential amplifier; $T_4$ and $T_5$ form the second stage differential complifier, Re is the constant current resistor; a voltage-regulator diode D controls the drain voltage of $T_1$ and $T_2$ to a proper level and at the same time works with $T_3$ to form a negative feedback of the amplifier to stabilize the working point of $T_1$ and $T_2$; $T_6$ forms an emitter follower as the output stage of the circuit wherein $r_1$ and $r_2$ are used to prevent parasitic oscillation. When the circuit shown in FIG. 5B is built up by independent elements, the characteristics of $T_1$ and $T_2$ should be well matched, for this purpose, the junction field effect transistor 2N4416 or 2N3823 manufactured by TEXAS INSTRUMENTS Corp. or 3DJ series (such as 3DJ2F) manufactured in China can be used, and it is required that the gate current $ig \leq 10^{-12}$ A. In FIG. 5B, a switch S and a parallel resistor network N form a feedback circuit which scales this amplifying circuit according to ten based exponential of the detected current and the relationship between input and output within each scale is linear.

Figure 6:
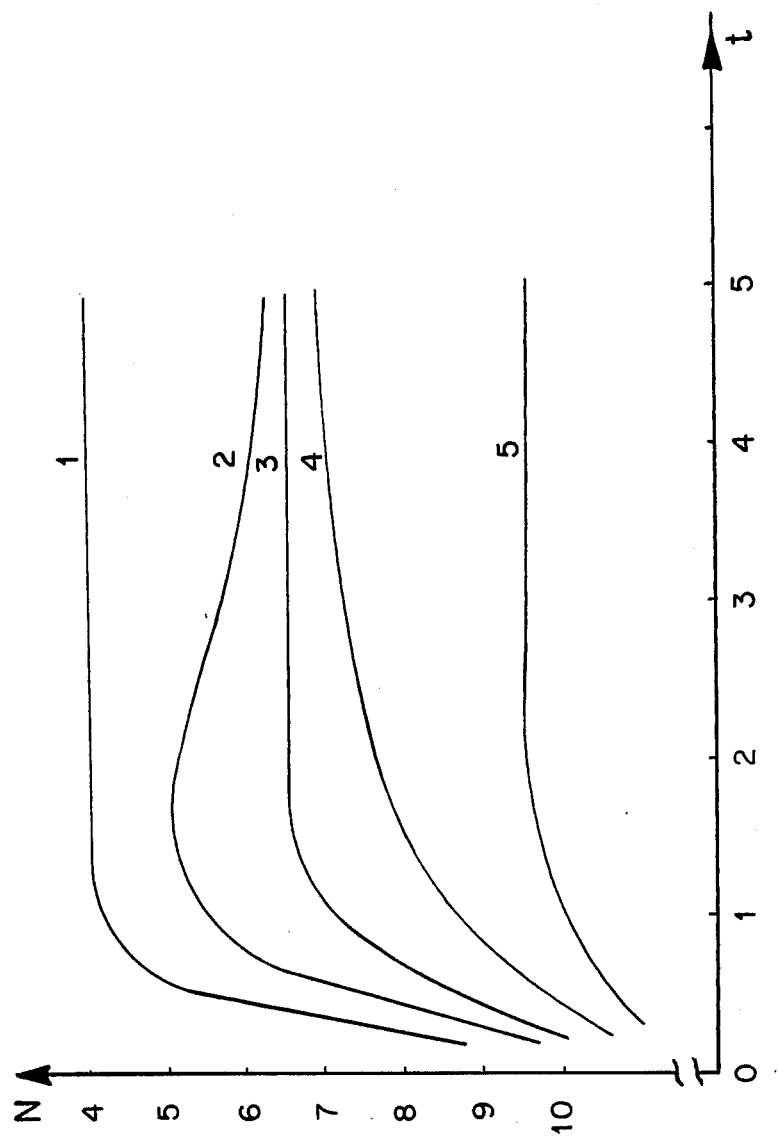
FIG. 6 shows the time response curves, detected under certain stimulating voltage, corresponding to the people having different health problems.

It is shown in FIG. 6 the time response curves of the current detected from several groups of patients. The detection is made by using the apparatus of the invention under same conditions to people having different diseases that have been diagnosed by other clinical means, and the detection is made by using a 2.0 V step signal as the stimulating voltage. In FIG. 6, the abscissa represents time in term of second with its zero point corresponding to the leading edge of the step signal, while the ordinate represents the negative logarithmic value N of the response current. In FIG. 6, the five curves correspond to five groups of people which are the same as that of FIG. 3, namely, curve 3 is detected from a group of normal control group, curve 1 is detected from a group of patients having manic mental disorders, curve 2 is detected from a group of patients having slight autonomic nerve system disorders, curve 4 is detected from a group of patients having slight metabolic disorders, and curve 5 is detected from a group of patients having cancers at advanced stage. It can be seen from the curves shown in FIG. 6 that when the detecting apparatus of the invention is used for detection at specific acupoints, it can be found a time-related change of the response current which occurs in different way for patients having different disease, hence the current's change over time can also be helpful in diagnosis. It is shown in FIG. 6 that the time response curves of the patients having serious deseases (curves 1 and 5) have significant differences from that of normal control (curve 3), but the curves of the patients having slight disorders (curves 2 and 4) have a tendency of getting closer to that of normal control with time. It can be seen from the data of FIG. 6 that within the range of 1-2 second, the values of response current detected from different patients manifest most distinguishable differences. Accordingly if a sample-and-hold circuit is used for sampling the response current, the sampling time should be delayed 1-2 seconds, preferably 1.5 seconds, from the leading edge of the stimulating signal. It should be pointed out that the data shown in FIGS. 2 and 3 are all sampled at a delay time of 1.5 seconds. On the other hand, if the curves shown in FIG. 6 are sampled at a multiple of points, information about the rising slope, peak value and declining slope of the time response curves can be obtained which are useful in diagnosing diseases and determining seriousness of a disease.

Figure 7A:
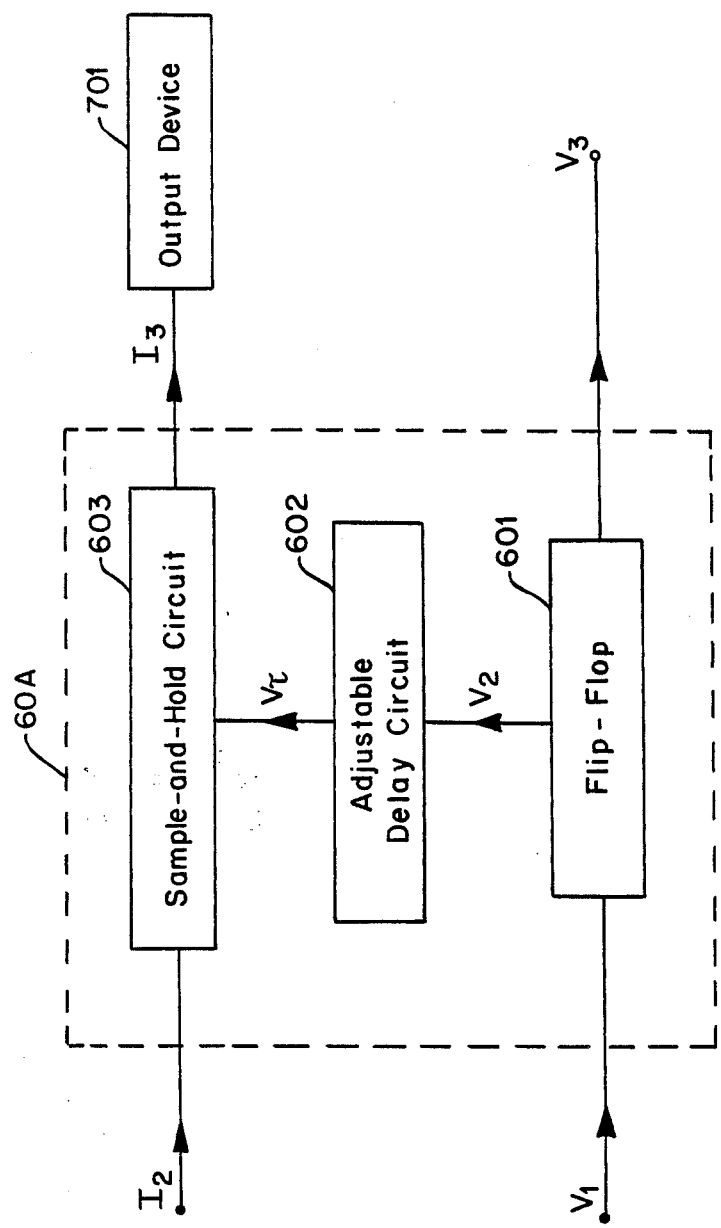
FIGS. 7A-7B show respectively two different embodiments of the signal processing circuit 60 shown in FIG. 1.

Referring to FIG. 7A, there is shown an embodiment of the signal processing circuit 60 shown in FIG. 1, which is characterized in that it samples the time response curve at a predetermined time to obtain useful information therefrom according to the features of the curves shown in FIG. 6. In FIG. 7A, the dash line block 60A represents the signal processing circuit as a whole, numeral 601 indicates a flip-flop which has an input signal $V_1$ from a triggering switch of the detecting electrode 20 and will generate two output signals $V_2$ and $V_3$ when it is activated by signal $V_1$. Signal $V_3$ is provided to the stimulating signal generating circuit 40 shown in FIG. 4 for controlling the generation of the stimulating signal; while signal $V_2$ is provided to an adjustable delay circuit 602 for controling the generation of a sampling frequency signal $V_\tau$. Numeral 603 indicates a sample-and-hold circuit which, under the control of the sampling frequency signal $V_\tau$, samples the amplified signal $I_2$ which is the output of the micro-current amplifying circuit 50 shown in FIG. 1 and corresponds to the micro-current signal $I_1$. The sampled signal is provided to an output device 70 as signal $I_3$. Since all the blocks shown in the FIG. 7A are known in prior art, they will not be further described.

Figure 8:
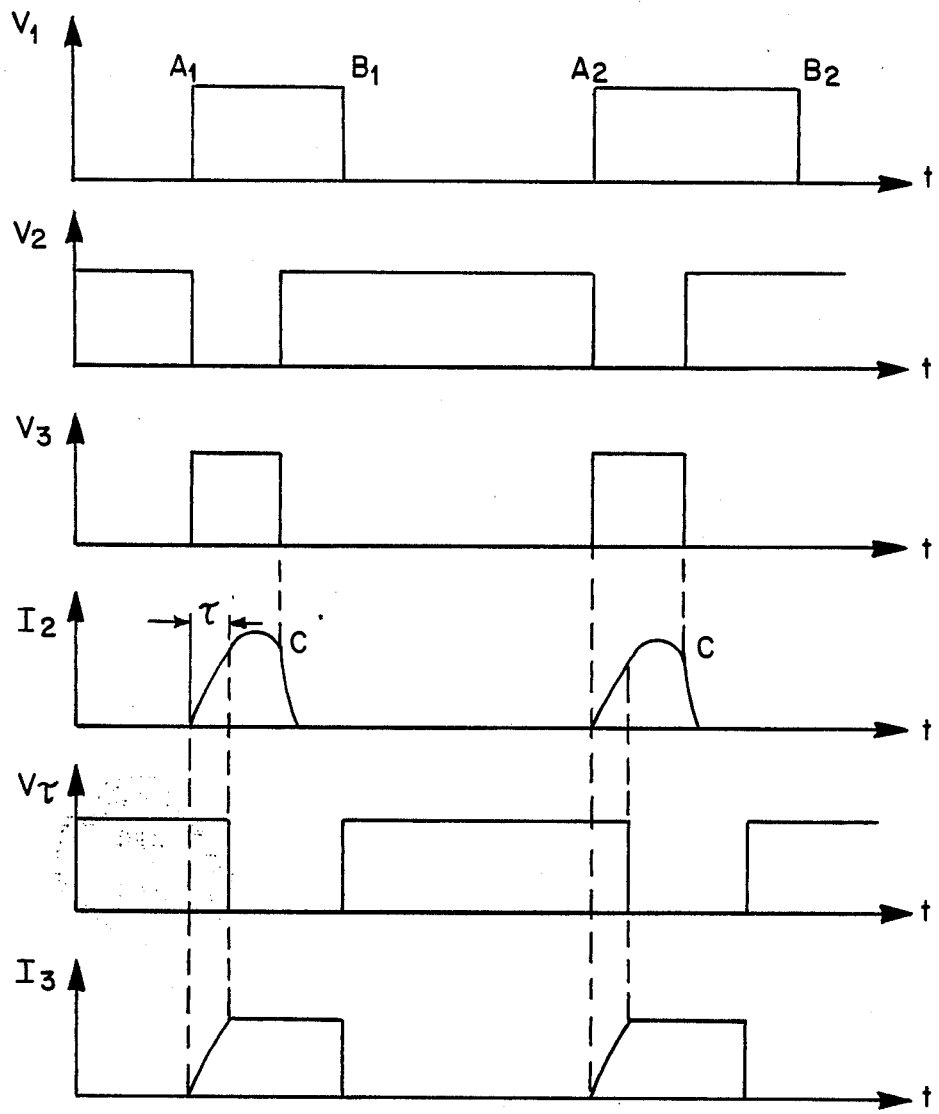
FIG. 8 shows the waveform on the nodes shown in FIG. 7A.

FIG. 8 shows the waveform of the signals on corresponding nodes in FIG. 7A, wherein $V_1$ is an activating signal provided by an triggering switch in the detecting electrode which will be further described later. The leading edge $A_1$ of the activating signal is determined by the manipulating of the user to the detecting electrode, the width between $A_1$ and $B_1$ is determined by the time the detecting electrode is kept at an acupoint on patient's body; the interval between $A_1$ and next activating signal $A_2$ is also determined by user's manipulating for next acupoint. So both the width of each activating signal and the interval between two such signals are determined by manipulating the apparatus. $V_2$ indicates negative pulses generated by the flip-flop 601; the width of these pulses is predetermined to meet the need of the circuit 603, and their leading edge is determined by that of $V_1$, such as $A_1$ and $A_2$. $V_3$ indicates the positive pulses generated by the flip-flop 601, which controls the generation of a step or pulse signal by circuit 40 shown in FIG. 1. The width of $V_3$ is predetermined to meet the need of the sample and hold circuit 603. $I_2$ is the output of the amplifying circuit 50, which corresponds to the response current through a specific acupoint subjecting to the stimulating voltage, the waveform of $I_2$ corresponds to the curves shown in FIG. 6. The declining edge of $I_2$ at point C corresponds to the trailing edge of $V_3$. When the stimulating voltage becomes zero, $I_2$ declines according to an exponential curve. $V_\tau$ is the sampling frequency signal generated by the adjustable delay circuit 602, which is a negative pulse signal with its leading edge keeping a fixed delay i (for example, i=1.5 S) behind the leading edge of the negative pulse $V_2$, thereby to guarantee the sampling of time response curves shown in FIG. 6 is done on specific points. $I_3$ is the output of the sample-and-hold circuit 603, which can be displayed on output device 70 in analog or digital form. It should be pointed out that in the embodiment shown in FIG. 7A, the adjustable delay circuit 602 can be replaced by a time sequence circuit which generates a multiple of, instead of one, sampling frequency signals within the sampling interval $V_2$, and a multiplex sampling circuit can be adopted for performing multiplex sampling and parallel output, thereby obtaining the useful information such as the slope, and peak value of the time response curve.

Figure 7B:
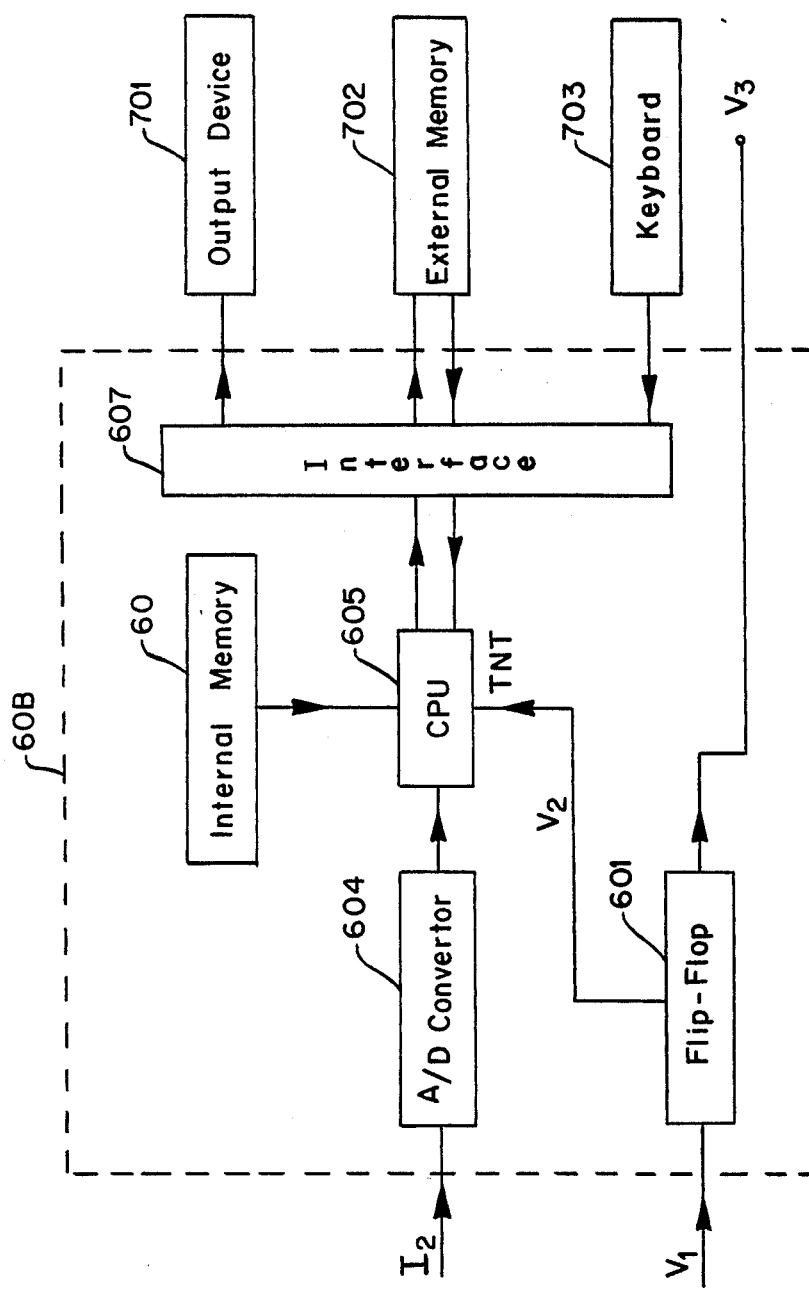

Referring to FIG. 7B, there is shown another embodiment of the signal processing circuit 60 shown in FIG. 1. Therein the dash line block 60B represents the signal processing circuit as a whole, numeral 601 indicates a flip-flop which is the same as that shown in FIG. 7A, numeral 604 indicates a A/D converter which convertes the analog output $I_2$ of the amplifying circuit 50 into a digital signal to be processed by a CPU 605. Activated by signal $V_2$, the CPU 605 processes the digital output of the A/D converter 604 according to an operating program stored in a memory 606 in advance, then provides it via an I/O interface 607 to output device 701. The output provided by the CPU 605 includes the time response curve of the current detected at an acupoint, the rising slope, peak value, declining slope thereof, the time when the peak value is reached, and the difference between the detected value and normal value, etc. Information such as the patient's name, age and sex, the code of detected acupoint, date, etc, can be inputted through a key-board 703 for storing and statistical processing at a later time; all the parts 701, 702 and 703 are known in the prior art and will not be further described. It should be pointed out that if only the time response curve is desirable, the output signal $I_2$ of the amplifying circuit 50 can be directly provided to a conventional oscilloscope or curve plotter, so they can be used to replace the signal processing circuit 60 and output device 70 for processing and displaying the curve. Since these devices are known to the prior art, they will not be further described.

Figure 9:
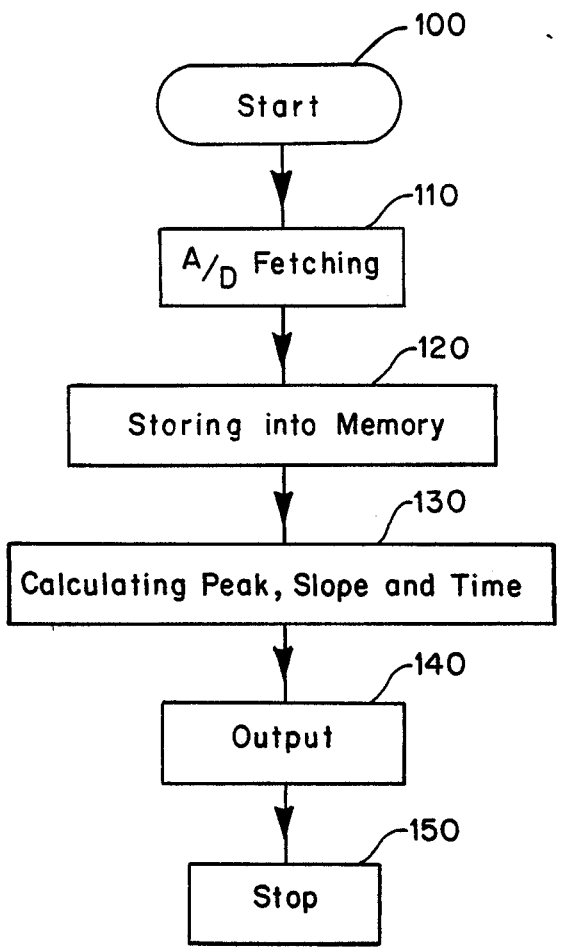
FIG. 9 shows a program flow chart used by the embodiment shown in FIG. 7B.

FIG. 9 shows the flow chart of the operating program of the CPU 605 of FIG. 7B. The program is initiated at step 100 by the leading edge of the signal $V_2$ provided by flip-flop 601; step 110 is a fetching step which fetches the digitalized signal from the A/D convertor 604; the fetched data is stored into an internal memory 606 for later use in a memory storing step 120; the parameters such as the rising slope, peak value, declining slope and the time of the peak value, of the time response curve are calculated from the fetched data at step 130, and the calculated parameters are further compared with the normal values stored in advance or kept for statistical processing; in step 140, the detected results are provided to output device 701 for displaying or printing, or to external memory 702 for storing; then the program enters the stop step 150. It should be noticed that as all these processing steps are known in the prior art, no further description will be given hereinbelow. In addition, further processing of the data provided by the present apparatus is within the scope of this invention and will not be described.

Figure 10:
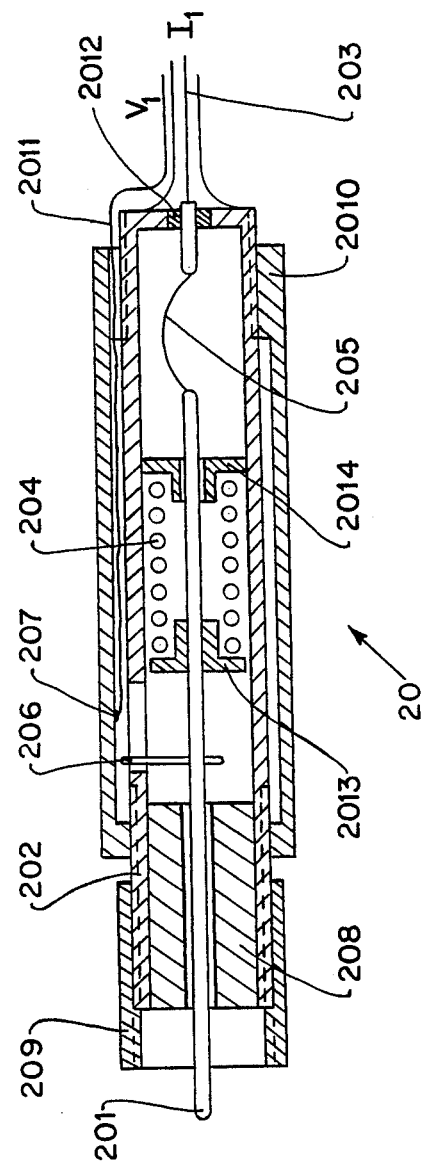
FIG. 10 is a diagram illustrating an exemplary embodiment of the detecting electrode 20 shown in FIG. 1.

Referring to FIG. 10, there is shown illustratively the structure of an exemplary embodiment of the detecting electrode 20 shown in FIG. 1. Therein, numeral 20 represents the detecting electrode as a whole; numeral 201 indicates a metal probe of a diameter in the range of 1.0–2.0 mm and a smooth end for a noninvasive contact with the acupoint skin; numeral 202 indicates a metal screen layer around the electrode which screens the whole mental probe 201 from environmental interference; numeral 203 indicates a coaxial cable with its inner conductor connected to the metal probe 201 and its outer conductor connected to the screen layer 202; numeral 204 indicates a spring with its one end fixed on the screen layer 202 through an insulating member 2014 and the other end fixed on the metal probe 201 through another insulating member 2013; and numeral 205 indicates a hairspring. By adopting a structure of the spring 204 and the hairspring 205, the mental probe 201 can perform a longitudinal movement relative to the screen layer 202, while it is biased by the spring 204 to return to its normal position. The hairspring 205 offers a good electrical connection during this movement. Accordingly, the pressure subjected at an acupoint is kept constant during detection by the spring 204. Numeral 206 indicates an insulated pin with its one end extending through a slot on the screen layer 202 and the other end fixed on the probe pin 206 can move together with the probe and close a switch 207 for providing an activating signal $V_1$ to the signal processing circuit 60 via line 2011. Numeral 208 indicates an insulated tube which insulates the probe 201 from the screen layer 202 as the probe moves longitudinally within it. Numeral 209 indicates an adjustable insulated tube which can be moved along the screen layer 202 through an engagement structure therebetween, so as to change the length of the part of the probe 201 extending out of the end face of the tube. When the probe contacts an acupoint's skin, both the far end of probe 201 and the front end of adjustable insulated tube 209 contact the skin, so the pressure subjected by skin is determined by the biassing force applied to the probe 201 by spring 204 when the probe moves back from its normal position to a position having its far end flush to the front end of the tube. If the tube 209 is adjusted backward along the screen layer 202, the part of the probe extending out of the tube 209 will be longer, so the pressure applied to an acupoint during detection will be larger, and vice versa. In this way, quantitative adjustment of the probe's pressure is provided. Numeral 2010 indicates an insulated housing of the detecting electrode, which insulates the screen layer from the user's hand to avoid interference from the by user's hand. Numeral 2012 indicates an insulating layer which insulates the line connected to the probe from the screen layer 202. It can be seen in FIG. 10 that the detected signal $I_1$ is through the inner conductor of the coaxial cable while the activating signal $V_1$ is through the line 2011, to avoid the interferences therebetween, and that the switch 207 and line 2011 are mounted outside the screen layer 202.

Figure 11:
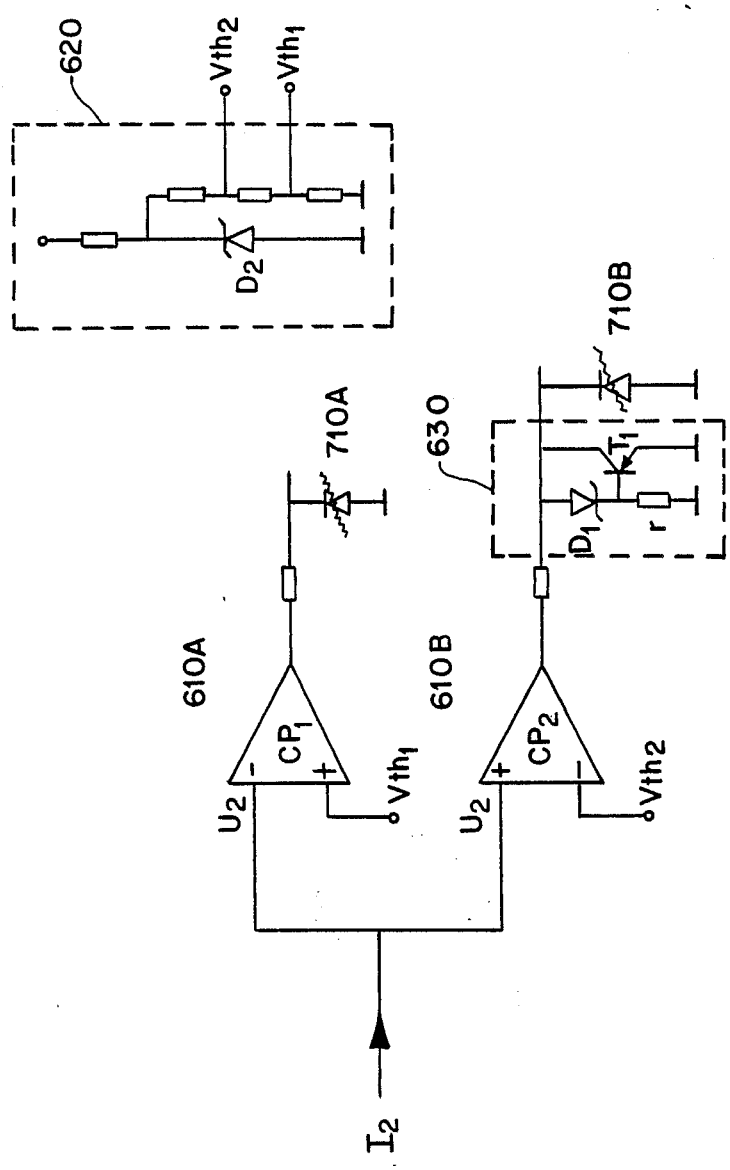
FIG. 11 is a circuit diagram illustrating the third embodiment of the detecting apparatus according to the present invention.

FIG. 11 shows another embodiment of the signal processing and displaying portion of the apparatus of the invention. In this embodiment, the signal processing circuit 60 shown in FIG. 1 comprises a pair of parallel comparators, and the output device 70 comprises a pair of light emitting diodes connected to one of the comparators respectively. A qualitative display of the detecting results is fulfilled by a very simple circuit of this embodiment. In FIG. 11, numeral 610 A indicates a first comparator with its inverted input connected to the output of the amplifying circuit 50, its non-inverted input connected to a threshold voltage Vth1, and its output connected to a light emitting diode (LED) 710 A. Numeral 610B indicates a second comparator with its non-inverted input connected to the output of the complifying circuit 50, its inverted input connected to a threshold voltage Vth2, and its output connected to a second LED 710B. There is a cut-off circuit 630 connected between the output of the second comparator 610B and the LED 710B which comprises a transistor $T_1$, a clamping diode $D_1$ and a resistor r. The first and second threshold voltages Vth1 and Vth2 are generated by a voltage dividing network 620, which comprises a clamping diode $D_2$ and a set of serially connected voltage dividing resistors. During detection, the output signal $I_2$ of the amplifying circuit 50 provides an input signal $U_2$ at both the inverted input of comparator 610A and the non-inverted input of comparator 610B, when $Vth1 < U_2 < Vth2$, the outputs of both the comparators 610A and 610B are negative, and two light emitting diodes are illuminated indicating that $U_2$ is within a normal range. When $U_2 < Vth1$, the output of comparator 610A is positive while that of 610B is negative, and LED 710A does not light but LED 710B is lit. When $U_2 < Vth2$, the output of comparator 610A is negative while that of 610B is positive, and the LED 710A is illuminated but LED 710B is not. By selecting the parameters of the circuit, Vth1 can be selected corresponding to a level of the micro-current $I_1 = 10^{-8}$ A, and Vth2 corresponding to a level of $I_1 = 10^{-6}$ A, then the above circuit can display when $I_1 < 10^{-8}$ A (710A does not illuminate, 710B does); $10^{-8} < I_1 < 10^{-6}$ A (both of 710A and 710B illuminate) and $10^{-6}$ A $< I_1$ (710A illuminate, 710B does not). In this way, the detected micro-current signal can be displayed qualitatively with the range of $10^{-8}$–$10^{-6}$ A as normal value. When the detecting loop is open, that means $I_2 = 0$ and $U_2 = 0$, the output of 610A is positive, and that of 610B is a saturated negative voltage which makes the clamping diode $D_1$ of the cut-off circuit 630 conductive. The transistor $T_1$ is then also conductive by the potential drop across the resistor r, so the LED 710B is cut off. Therefore when $U_2 = 0$, neither LED 710A or 710B will illuminate, and no error display will happen when the detecting loop is open.

It can be seen from the circuit shown in FIG. 11 that since it only displays the detecting results qualitatively, the requirements to the circuit and hence its cost are low, so it can be used by any patient for his daily use. On the other hand, since the step signal and the sample-and-holding circuit are not adopted in this embodiment, the user can have the detecting electrode moving continuously on the skin until an abnormal display happened. In this way, the apparatus can be used to locate acupoints with signal response which differs from the response elsewhere.

Figure 12:
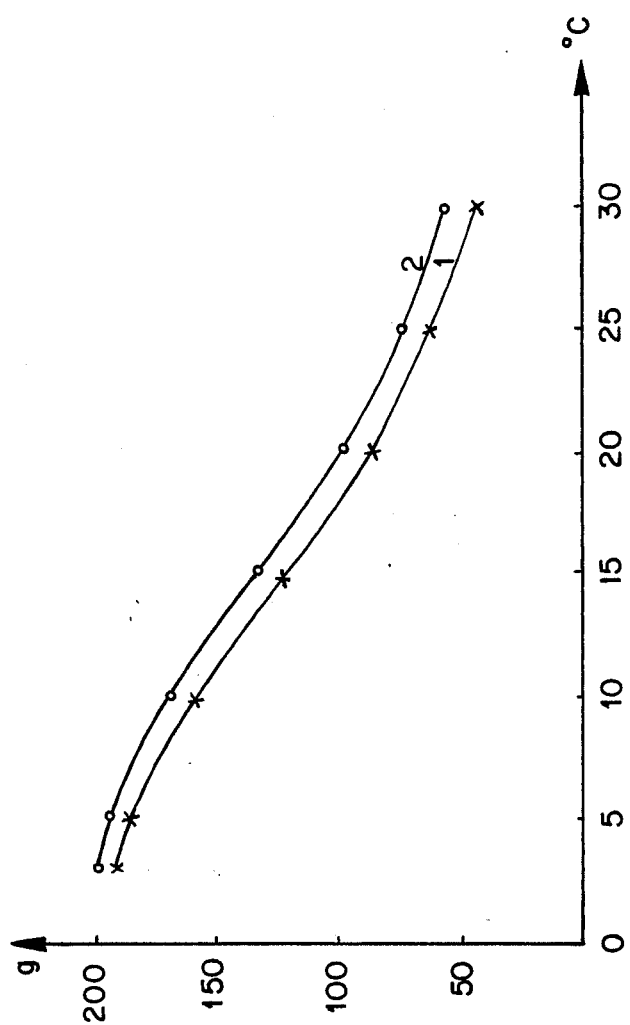
FIG. 12 shows the relationship between the pressure applied to the skin point by the detecting electrode of the invention and the environmental temperature and humidity.

FIG. 12 illustrates the relationship between the pressure applied to acupoint skin by the detecting electrode of the invention and the environmental temperature and humidity. As mentioned before, when the pressure applied to skin by the probe of the detecting electrode is varied, the accuracy of the detection will be influenced. On the other hand, environmental temperature and humidity will change the blood circulation in skin's microangium and skin's resistivity, these will also influence the accuracy of the detection. The detecting electrode of the invention can compensate the influence of the change of the temperature and humidity by adjusting the pressure applied to acupoint skin by the probe. The relationship between the pressure and the temperature is shown in FIG. 12, wherein the abscissa indicates the temperature in terms of degrees Centigrade (° C.), and the ordinate indicates the pressure in grams. The curve 2 in FIG. 12 corresponds to a lower humidity, when the humidity increases 20%, the pressure should be reduced 20 grams. In the detecting electrode of the invention, the force of the spring 204 is proportional to its pressed length, so the pressure applied to an acupoint by the probe can be quatitatively adjusted by altering the adjustable tube 209's position to change the probe's length extending out of the tube. The tube 209, shown in FIG. 10, can be even scaled to indicate the correspondence between temperature and position, based on the curve shown in FIG. 12.

It must be pointed out that except the detecting electrode shown in FIG. 10, an acupuncture needle can also be used as a detecting or reference electrode of the apparatus. Therefore it is convenient for an acupuncture doctor to use the apparatus of the invention in diagnosing and treating diseases. When a needle is used as the detecting and/or reference electrode, the skin resistance will not influence the detection made by this invasive electrode, and the stimulating voltage generated by the circuit 40 shown in FIGS. 1 and 4 should be selected about 0.5 V to obtain a substantially same detecting result.

The principles and structures of the apparatus for detecting bioelectrical signals of the present invention have been described in detail hereinbefore with reference to the drawing. It will be obvious to those skilled in the art to make many modifications and rearrangements of the above embodiments without departing from the spirit and scope of the invention; therefore, these embodiments are only used for illustrating and understanding the invention, and the scope of the present invention is determined only by the claims accompanyed hereinbelow.

We claim:

1. An apparatus for stimulating and detecting bioelectric signals, comprising:
    a detecting electrode, adapted to detect electrical signals when in contact with the skin of a patient at chosen acupoints on the body of the patient;
    a reference electrode adapted to be held against the skin of a patient and the couple stimulating signals into the skin of the patient at a fixed reference point on the center line of the patient;
    an amplifying circuit means connected to said detecting electrode for amplifying micro-current signals in the range of $10^{-11}$ and $10^{-4}$ amperes detected thereby:
    a stimulating signal generating circuit means connected to said reference electrode for applying a stimulating voltage to the skin of the patient at said fixed reference point on the center line of the body of the patient;
    wherein said detecting electrode, reference electrode, amplifying circuit means, and stimulating signal generating circuit means form a stimulating and detecting circuit means for stimulating and detecting bioelectric signals;
    the apparatus further comprising a signal processing circuit means connected to the output of said amplifying circuit means for processing the output signals; and
    output means connected to the output of said signal processing circuit means for displaying the processed output signals;
    wherein said amplifying circuit means comprises:
    a logarithmic micro-current amplifier;
    a temperature compensating circuit; and
    an inverting circuit;
    wherein said logarithmic micro-current amplifier has an input connected to said detecting electrode, and an output connected to an input of said temperature compensating circuit which has an output connected in turn to the input of said inverted circuit, and the output of the inverting circuit is provided to the input of said signal processing circuit means, whereby a detected micro-current in the range of $10^{-11}$–$10^{-4}$ amperes is amplified to provide an output signal proportional to the negative logarithm of said micro-current.

2. An apparatus for detecting bioelectric signals as claimed by claim 1, wherein said stimulating voltage generated by said stimulating signal generating circuit means is a DC voltage in the range 0.5–3.0 V.

3. An apparatus for detecting bioelectric signals as claimed by claim 1. wherein said amplifying circuit means comprises:
   a first differential amplifier;
   a second differential amplifier;
   an emitter follower; and
   a feedback circuit comprising a selecting switch and a resistor network;
   wherein said first differential amplifier has an input connected to said detecting electrode, and an output connected to the input of said second differential amplifier whose output is connected to the input of said emitter follower, which in turn provides its output to the input of said signal processing circuit means, said feedback circuit is connected between the input of said first differential amplifier and the output of said emitter follower, and the gain of the amplifying circuit means is changed by said selecting switch to perform an exponentially scaled linear amplification of a micro-current in the range of $10^{-11}$–$10^{-4}$ ampere.

4. The apparatus of claim 3, in further combination with means for storing amplified detected signals detected at a first chosen acupressure point for comparison to comparable detected signals.

5. The apparatus of claim 4, wherein said comparable signals are detected with respect to different points on the same patient, the same points on different patients, or the same point on the same patient at a different time.

6. An apparatus for stimulating and detecting bioelectric signals, comprising:
   a detecting electrode, adapted to detect electrical signals when in contact with the skin of a patient at chosen acupoints on the body of the patient;
   a reference electrode adapted to be held against the skin of a patient and to couple stimulating signals into the skin of the patient at a fixed reference point on the center line of the patient;
   an amplifying circuit means connected to said detecting electrode for amplifying micro-current signals in the range of $10^{-11}$ and $10^{-4}$ amperes detected thereby:
   a stimulating signal generating circuit means connected to said reference electrode for applying a stimulating voltage to the skin of the patient at said fixed reference point on the center line of the body of the patient;
   wherein said detecting electrode, reference electrode, amplifying circuit means, and stimulating signal generating circuit means form a stimulating and detecting circuit means for stimulating and detecting bioelectric signals;
   the apparatus further comprising a signal processing circuit means connected to the output of said amplifying circuit means for processing the output signals; and
   output means connected to the output of said signal processing circuit means for displaying the processed output signals;
   wherein said detecting electrode comprises:
   an inner conductor;
   an outer conductor which shields said inner conductor;
   a coaxial cable with its inner and outer conductors connected respectively to said inner and outer conductors;
   an insulating layer which insulates said inner and outer conductors from each other at their detecing ends;
   wherein during detection said inner conductor forms a noninvasive contact with the skin of the patient while said outer conductor is insulated from said skin.

7. An apparatus for detecting bioelectric signals as claimed by claim 6, where said detecting electrode comprises:
   an elastic member which is insulated from and fixed at its two ends to said inner and outer conductors, respectively, whereby said inner conductor is longitudinally movably relative to said outer conductor, whereby a constant pressure is applied to a point on said skin by said conductor.

8. An apparatus for detecting bioelectric signals as claimed by claim 7, wherein said detecting electrode comprises:
   means for adjusting pressure, which is mounted on the detecting end of said outer conductor with its position adjustable along the length of said outer conductor, thereby to change the movable length of said inner conductor relative to said outer conductor and hence the pressure applied to a point on said skin by said elastic member via said inner conductor.

9. An apparatus for detecting bioelectric signals as claimed by claim 7, wherein said detecting electrode further comprises a triggering switch which generates an activating signal when said inner conductor contacts an acupoint with a certain pressure;
   said signal processing circuit means comprising a flip-flop connected to said triggering switch, to generate control signals for said signal processing circuit means and said stimulating signal generating circuit means according to said activating signal; and
   said stimulating signal generating circuit means comprising a circuit controlled by said flip-flop for generating said stimulating signal.

10. The apparatus of claim 6 wherein said stimulating voltage is a DC voltage in the range of 0.5–3.0 v.

11. An apparatus for stimulating and detecting bioelectric signals, comprising:
   a detecting electrode, adapted to detect electrical signals when in contact with the skin of a patient at chosen acupoints on the body of the patient;
   a reference electrode adapted to be held against the skin of a patient and to couple stimulating signals into the skin of the patient at a fixed reference point on the center line of the patient;
   an amplifying circuit means connected to said detecting electrode for amplifying micro-current signals in the range of $10^{-11}$ and $10^{-4}$ amperes detected thereby:
   a stimulating signal generating circuit means connected to said reference electrode for applying a stimulating voltage to the skin of the patient at said fixed reference point on the center line of the body of the patient;
   wherein said detecting electrode, reference electrode, amplifying circuit means and stimulating signal generating circuit means form a stimulating and detecting circuit means for stimulating and detecting bioelectric signals;

the apparatus further comprising a signal processing circuit means connected to the output of said amplifying circuit means for processing the output signals; and output means connected to the output of said signal processing circuit means for displaying the processed output signals;

wherein said signal processing circuit means comprises:

a delay circuit; and a sample-and-hold circuit;

wherein said sample-and-hold circuit samples the output signal of said amplifying circuit means with a fixed delay time under the control of said delay circuit and holds the sampled signal for providing it to said output means.

12. An apparatus for detecting bioelectric signals as claimed by claim 11, wherein said signal processing circuit means further comprises:

an A/D convertor;

A CPU;

a memory;

an interface circuit; and a key-board;

wherein said A/D convertor has its input connected to the output of said amplifying circuit means to convert the analog signal therefrom into a digital signal, which is sent to said CPU said CPU processes said digital signal according to a operation routing stored in said memory and instructions inputted through said key-board, and the processed results are sent to said output means via said interface circuit.

13. An apparatus for detecting bioelectric signals as claimed by claim 12, wherein said detecting electrode further comprises a triggering switch which generates an activating signal when said inner conductor contacts an acupressure point with a certain pressure;

said signal processing circuit means further comprises a flip-flop connected to said triggering switch for providing an initiating signal to said CPU upon receiving the activating signal, to start the processing routine of said CPU to process the detected signals; and said stimulating signal generating circuit means comprises a circuit controlled by said flip-flop for generating said stimulating signal.

14. An apparatus for detecting bioelectric signals as claimed by claim 11, wherein said detecting electrode further comprises a triggering switch which generates an activating signal when said inner conductor contacts said acupressure point with a certain pressure;

said signal precessing circuit means further comprises a flip-flop connected to said triggering switch for providing a control signal to said delay circuit upon receiving the activating signal, to cause said delay circuit to generate a delay signal; and said stimulating signal generating circuit means comprises a circuit controlled by said flip-flop for generating said stimulating signal.

15. An apparatus for detecting bioelectric signals as claimed by claim 11, wherein said delay circuit provides an output signal for controlling said sample-and-hold circuit to sample the output signal of said amplifying circuit means with a fixed delay time in the range of 1.0–2.0 second, and holds the sampled signal for output.

16. An apparatus for stimulating and detecting bioelectric signals, comprising:

a detecting electrode, adapted to detect electrical signals when in contact with the skin of a patient at chosen acupoints on the body of the patient;

a reference electrode adapted to be held against the skin of a patient and to couple stimulating signals into the skin of the patient at a fixed reference point on the center line of the patient;

an amplifying circuit means connected to said detecting electrode for amplifying micro-current signals in the range of $10^{-11}$ and $10^{-4}$ amperes detected thereby:

a stimulating signal generating circuit means connected to said reference electrode for applying a stimulating voltage to the skin of the patient at said fixed reference point on the center line of the body of the patient;

wherein said detecting electrode, reference electrode, amplifying circuit means, and stimulating signal generating circuit means form a stimulating and detecting circuit means for stimulating and detecting bioelectric signals;

the apparatus further comprising a signal processing circuit means connected to the output of said amplifying circuit means for processing the output signals; and output means connected to the output of said signal processing circuit means for displaying the processed output signals, wherein said signal processing circuit means comprises:

a threshold voltage dividing circuit having two outputs providing respectively upper and lower threshold signals;

a pair of comparators connected to compare the output of said amplifying circuit means to said upper and lower threshold signals to determine the range of said output signal;

display means connected to the outputs of said comparators to display the comparison result determined by the output signals to said comparators; and a cut-off circuit which cuts off the output of said comparators when the output signal of said amplifying circuit means is zero, to stabilize the output of said display means.

17. A method for treating a patient, comprising the steps of placing a reference electrode against the skin of the patient at a fixed reference point on the center line of the body of the patient;

applying a stimulating signal to the body of the patient at said fixed reference point by way of said reference electrode;

successively placing a detecting electrode against the skin of the patient at a series of chosen acupoints on the body of the patient;

detecting electrical currents passing from said reference electrode into the body of said patient at said fixed reference point, through the body of said patient, and into said detecting electrode at said series of chosen acupoints, said signal typically being a micro current in the range of $10^{-11}$–$10^{-4}$ amperes;

amplifying said detected signals; and recording the currents detected at each of said chosen acupoints on the body of the patient, for comparison to comparable micro current signals detected similarly at others of said acupoints on the body of said patient, at the same and other acupoints detected on the body of said patient at other times, and at the same and other acupoints on the bodies of other patients for diagnosis and treatment of said patient.

18. The method of claim 17, wherein said stimulating signal is a voltage in the range of 0.5–3.0 V.

* * * * *